United States Patent [19]
Khalil et al.

[11] Patent Number: 5,089,424
[45] Date of Patent: Feb. 18, 1992

[54] METHOD AND APPARATUS FOR HETEROGENEOUS CHEMILUMINESCENCE ASSAY

[75] Inventors: Omar S. Khalil, Libertyville; Thomas F. Zurek, River Forest; Kevin R. Genger, Chicago; Curtis J. Pepe, McHenry; Yi-Her Jou, Vernon Hills; Stephen M. Cotter, Fox Lake, all of Ill.

[73] Assignee: Abbott Laboratories, Abbott Park, Ill.

[21] Appl. No.: 425,643

[22] Filed: Oct. 23, 1989

Related U.S. Application Data

[63] Continuation-in-part of Ser. No. 206,645, Jun. 14, 1988, abandoned.

[51] Int. Cl.⁵ ............................. G01N 33/543
[52] U.S. Cl. ........................... 436/518; 436/530; 436/537; 422/56; 422/58; 422/57; 422/61
[58] Field of Search ............ 436/530, 537, 518; 422/56–58, 61

[56] References Cited

U.S. PATENT DOCUMENTS

| | | |
|---|---|---|
| 3,992,158 | 11/1976 | Przybylowicz . |
| 4,363,874 | 12/1982 | Greenquist . |
| 4,552,839 | 11/1985 | Gould et al. . |
| 4,623,461 | 11/1986 | Hossom et al. ............... 422/101 |
| 4,632,901 | 12/1986 | Valkirs et al. . |
| 4,652,533 | 3/1987 | Jolley et al. ............... 422/56 |

FOREIGN PATENT DOCUMENTS

| | | |
|---|---|---|
| 0131934 | 1/1985 | European Pat. Off. . |
| 0200381 | 11/1986 | European Pat. Off. . |
| 2245797 | 9/1972 | Fed. Rep. of Germany . |

OTHER PUBLICATIONS

Kang et al., Clin. Chem., 32, 1682–1686 (1986).
Schroeder et al., Clin. Chem., 27, 1378–1384 (1981).
John B. Birks, *Photophysics of Aromatic Molecules*, Chapter 2, Photophysical Processes, Wiley-Interscience, N.Y. 1970.

*Primary Examiner*—Robert J. Warden
*Assistant Examiner*—Lyle A. Alexander
*Attorney, Agent, or Firm*—Priscilla E. Porembski; Daniel W. Collins

[57] ABSTRACT

Apparatus and method for performing a chemiluminescence assay involving the immobilization of a chemiluminescent reaction complex to a solid, porous element. The solid, porous element is preferably treated to provide an immobilizing interaction with the chemiluminescent reaction complex wherein the chemiluminescent reaction complex is thereby immobilized to the solid, porous element. The activating and reading of the chemiluminescent reaction are separately performed by evenly distributing a concentrated chemiluminescent activating solution to form a puddle on the surface of the porous element to which the chemiluminescent reaction complex is immobilized.

21 Claims, 7 Drawing Sheets

METHOD AND APPARATUS FOR HETEROGENEOUS CHEMILUMINESCENCE ASSAY

This application is a continuation-in-part application of U.S. Ser. No. 07/206,645, now abandoned entitled METHOD AND APPARATUS FOR HETEROGENEOUS CHEMILUMINESCENCE IMMUNOASSAYS, which enjoys common ownership and is incorporated herein by reference.

BACKGROUND OF THE INVENTION

The present invention relates to methods and apparatus for measuring a chemiluminescent signal from a solid surface. In particular, the present invention relates to methods and apparatus for use in heterogeneous immunoassays wherein a chemiluminescent signal provided by the immobilized product of an immunochemical reaction from a solid, porous matrix is measured.

Several automated chemiluminescence instruments use photographic means and a densitometer for recording signal. Vogelhut, U.S. Pat. No. 4,231,754; Whitehead, et al., U.S. Pat. No. 4,593,728; Thorpe, et al., *Clin. Chem.*, 30, 806, (1984); and Bunce, et al., *Analyst*, 110, 65 (1985).

Clear coated microtitration plates as a solid phase with trigger solution port and detector at opposite sides of the plate well may also be employed in such instruments. Holley, European Patent Application 025,350; and Schroeder, et al., Clin. Chem., 27, 1378-1384 (1981). This technique is severely limited due to the slow reaction rates resulting from the limited diffusion of analyte molecules to the capturing solid phase. Use of this approach has been of limited sensitivity and is generally employed in reactions involving the use of ATP and luminol-type tracers.

Magnetizable microparticles and magnetic separation in a test tube may be followed by reading the signal of the suspended particles in a tube luminometer as is found in the commercially available Magic TM Lite system distributed by Ciba-Corning Diagnostics. Because the brown colored microparticles optically interfere with the chemiluminescent signal, a very low mass of these particles is used. This leads to very slow reactions. For example, an assay for thyroid stimulating hormone (TSH) is reported to have a three-hour incubation time. In addition, many manipulation steps are involved, making this assay configuration difficult to automate. Other luminometers in which the signal is generated in a test tube are sold by Berthold, Hamilton, Turner Design and Analytical Luminescence.

Enhanced chemiluminescent reactions in a white microtitration plate followed by reading the generated signal in a luminometer having a moving mask and photomultiplier tube are described in Lisenbee, et al., European Patent Application 194,102 and are incorporated in the Amerlite TM system sold by Amersham Inc. This latter technique suffers from the same limitations of an ELISA assay in a coated plate, namely the slow diffusion rate of the reactants to the capture phase.

SUMMARY OF THE INVENTION

The present invention provides a method for directly exciting and measuring a chemiluminescent signal emanating off an immune complex immobilized on or in a solid, porous element that is used as a separation means in a heterogeneous immunoassay and an apparatus for performing this measurement. More specifically, it provides an automated means for performing heterogeneous chemiluminescent immunoassays of high sensitivity.

The present invention provides a method and apparatus for measuring a chemiluminescent signal produced by an immobilizable immune complex comprising analyte from a test sample which is capable of being immobilized by a solid, porous element. In particular, analyte is captured in a liquid phase using microparticles or polyionic capture agents having a binding affinity for the analyte wherein the captured analyte is subsequently immobilized by the porous element and a chemiluminescent signal is chemically excited and detected. Accordingly, the method of the present invention advantageously employs fast diffusion rates in solution to provide highly sensitive assays for a wide range of analytes.

The apparatus for performing a chemiluminescent assay according to the present invention includes a container having an aperture and a solid, porous element, preferably in the form of a fibrous matrix, capable of immobilizing a chemiluminescent generating reaction product complex while, at the same time, permitting the passage of other reaction components which are not immobilized by the porous matrix. The reaction product is immobilized by the porous element through particulate reactants or as the result of an interactive property between the porous element and the reaction product, such as hydrophilic-hydropholic binding interactions, ionic binding interactions, and the like. A detection device is situated adjacent to the container which moves to create a light-tight seal with the container to allow low light level chemiluminescence measurements. The detection device includes means for evenly distributing a chemiluminescent activating solution to the porous element. The aperture may be funnel-shaped and the means for applying the activating solution may include ports disposed toward an interior surface of the funnel.

The various methods known in the art for forming heterogeneous binding reaction systems can be followed in applying the method and apparatus of the present invention where a chemiluminescent label is employed as the labeled reagent. Typically, the assay reagents for performing such assays may take many different forms, but, in general, comprise (1) the analyte to be detected, (2) a specific binding partner for the analyte, and (3) a labeled reagent, which can be the same or different as the binding partner for the analyte. The assay reagents are generally combined simultaneously, or sequentially, wherein the labeled reagent becomes bound to its corresponding binding partner such that the extent of binding is a function of the amount of analyte present. Typically, the bound species and the free species are physically separated from each other and the amount of label present in either fraction thereof is determined by measuring the activity of the particular label being used. Such methods include those known as the competitive immunoassay binding technique, the sandwich immunoassay technique, and the immunometric technique. In all of these heterogeneous immunoassay systems, separation of the free and bound species of the labeled reagent is normally accomplished by immobilizing one of such species.

A method for performing a chemiluminescent assay according to the present invention includes the steps of binding an analyte to a chemiluminescent complex, binding the analyte-chemiluminescent complex to a particulate support having binding sites for the analyte-chemiluminescent complex to form an immobilizable reaction complex, contacting the immobilizable reaction complex with the porous element, and evenly distributing a chemiluminescent activating solution on the porous element to provide a chemiluminescent signal which is measured and correlated to the amount of analyte in a test sample.

Preferably, a method for performing a chemiluminescent assay according to the present invention includes the steps of binding an analyte to a chemiluminescent complex, building the analyte-chemiluminescent complex to an ionic moiety to form an immobilizable charged reaction complex, and contacting the charged reaction complex, with a solid, porous element having an ionic charge opposite to that of the immobilizable charged reaction complex whereby the charged reaction complex is immobilized by the solid, porous element as a result of the ionic binding interaction therebetween. A chemiluminescent activating solution is then evenly distributed on the porous element to provide a chemiluminescent signal which is measured and correlated to the amount of analyte in a test sample.

BRIEF DESCRIPTION AND DRAWINGS

FIG. 1: Side view of the chemiluminescent detection device according to the present invention.

FIG. 2: Isometric view of a preferred configuration of the detection head of the detection device according to the present invention.

FIG. 3: Cross-sectional view of the detection head shown in FIG. 2.

FIG. 4: Cross-sectional view taken along the perpendicular axis of the detection head shown in FIG. 2.

FIG. 5: Exploded view of the bottom of the detection device according to the present invention.

FIG. 6: Perspective view of the lifter mechanism of the detection device according to the present invention.

FIG. 7: A schematic diagram of the detection device according to the present invention.

DETAILED DESCRIPTION

Figure 1:
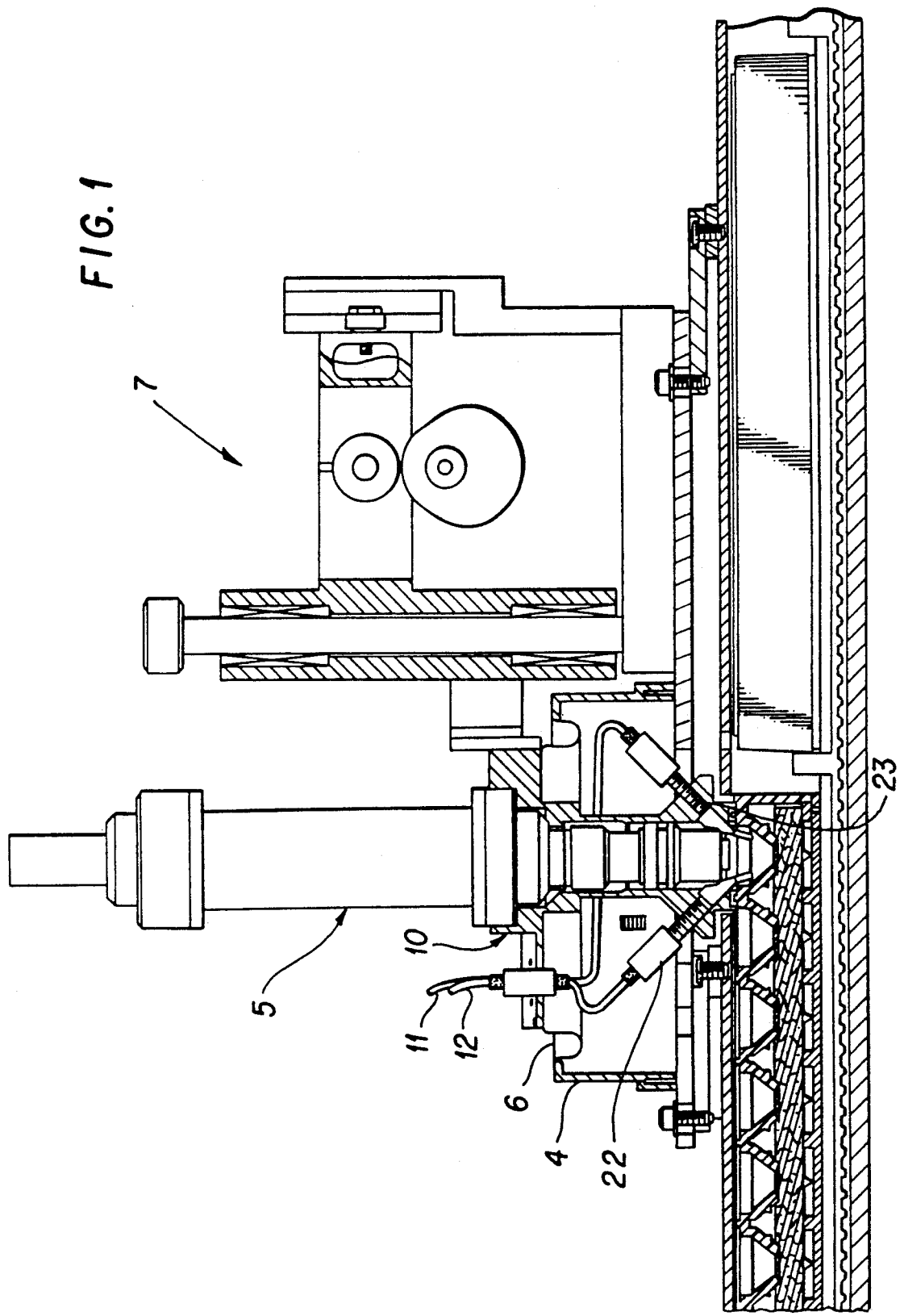

According to the present invention, heterogeneous chemiluminescent immunoassays may be easily automated, and hence their precision and accuracy improved, by generating and directly detecting a chemiluminescent signal from the separated reaction complex immobilized on a solid, porous element without the need to transfer the separated complexes to a tube or use a tube luminometer. The primary capture reaction is performed in the liquid phase to make use of the improved diffusion conditions in the liquids, and the immobilizable reaction complex is immobilized by the porous element as a result of an interaction between the immobilized reaction complex and the porous element, such as a hydrophobic interaction, anionic interaction, and the like. The chemiluminescence signal is generated from the porous element and is detected by a detector facing one side of the porous element and in close proximity to it, while the reaction products which are not immobilized, i.e. chemiluminescent binding complex not bound to the analyte, are disposed of by an absorbant matrix pad in intimate contact with the other side of the porous element. The porous element is an integral part of a disposable device that comprises reaction chambers and separation and detection chambers. The detector device has a shroud which surrounds the separation and detection chamber and creates a local light-tight compartment where a chemiluminescence signal is generated and detected. Either shroud or the whole assembly are movable in the Z-direction to affect a light-tight seal.

The solid, porous element of the present invention is preferably in the form of a fibrous matrix and is used to immobilize the immobilizable reaction complex as a result of the interaction therebetween, from which an assay signal can be generated. The porous element can be selected from woven fibrous materials such as glass, cellulose, nylon or other natural or synthetic material known to those skilled in the art. It can be also chosen from porous glass or ceramic fritted disks or polymer fritted disks. Material choice, dimensions and pore size of these porous elements can be easily selected by those skilled in the art, to provide an effective pore size and adequate void areas to permit proper flow of unreacted reagents and sample through the porous element.

Where the porous element is employed in an ion capture procedure, it is treated with a water soluble polycationic polymer. Choice of the water soluble polycation, amount of polymer, method and application can be determined by those skilled in the art. Derivatization of the surface of the porous element to generate positively charged groups and application of surface treatment techniques such as plasma treatment can also be contemplated and used by those skilled in the art. An important criterion is that the porous element is made from translucent or white material thus it will not absorb or attenuate the emitted chemiluminescent signal.

A preferred fibrous materials is H&V product No. HC 4111 glass fiber filter paper, which has a nominal thickness of 0.055 inches and is commercially available from Hollongsworth and Vose Co., East Walpole, Mass. The effective pore size of the fibrous matrix or the spatial separation of the fibers is chosen to be larger than the diameter of the microparticles employed in the assays. Spatial separation of larger than 10 microns is preferred. This is to assure that even after the immobilizable reaction complex is immobilized on the fibers, adequate void areas still exist for proper flow of reagents and sample through the fibrous matrix, which in turn prevents fluid retention on the surface of the matrix which, for example, protects the detection device against possible trigger solution splashing.

Ion capture procedures for immobilizing an immobilizable reaction complex with a negatively charged polymer tail, as described in copending U.S. patent application Ser. No. 150,278, entitled "Ion Capture Assays and Devices," filed Jan. 29, 1988, both of which are incorporated by reference herein, can be employed according to the present invention to affect a fast solution-phase immunochemical reaction. An immobilizable immune complex is separated from the rest of the reaction mixture by ionic interactions between the negatively charged poly-anion/immune complex and the previously treated, positively charged porous element and detected by the method described in the present invention.

Acridinium sulfonamides labeling chemistry, as described in copending U.S. patent application Ser. No. 371,763 entitled "Chemiluminescent Acridinium Salts", filed June 23, 1989, incorporated herein by reference, may be employed according to the present invention for making a stable luminescent tracer of high quantum yield.

Alkaline phosphatase labeling techniques known in the art and use of dioxetane catalyzed chemiluminescence may be also used according to the present invention to generate a long-lived signal that can be integrated to yield high sensitivity assays.

Chemiluminescent moieties can be used as probes or labels in a specific binding assay. For example, such chemiluminescent label can directly react with an activating reagent to generate a light signal, such as acridinium sulfonamides. Alternatively, such chemiluminescent label serves as a catalyst to accelerate the generation of light from a substrate, such as alkaline phosphatase, peroxidase and beta-galactosidase.

The combination of these techniques are particularly useful to permit a simple, rapid, highly sensitive immunoassay method for the determination of viral particles, macromolecular antigens and haptens. One such assay for Hepatitis B Surface antigen has sensitivities which exceed those of other methods. For example, one such type of chemiluminescence immunoassay for Hepatitis B surface antigen (*Clin. Chem,* 27, 1378-1384, 1981) involves two incubation periods, 1.5 hours each, and has a lowest limit of detection of 2 ng/mL. A lowest limit of detection of 1 ng/mL is achieved by increasing the incubation time to 16 hours. Using the method and detection device described according to the present invention, sub-nanogram quantities of Hepatitis B surface antigen may be detected within a total assay time of less than one hour.

According to a preferred embodiment of the present invention, a sandwich immunoassay is performed employing a polyanionic acid such as polyglutamic acid which is attached to an antibody to the analyte under determination, and added to a reaction vessel, either simultaneously or sequentially, with the analyte from a test sample and a chemiluminescent-labeled antibody. The reaction mixture is incubated for a period of time and under conditions which maximize the specific binding reaction. The reaction mixture is transferred to a separation and detection chamber. Transfer of the reaction mixture into the separation and detection chamber can be achieved by mechanical means such as a manual or automated pipettor or by a non-contact hydraulic or fluidic means such as described by co-pending U.S. patent application Ser. No. 184,726, entitled "Device and Methods for Performing a Solid-Phase Immunoassay", filed Apr. 22, 1988, incorporated herein by reference.

The chemiluminescence signal from acridinium labeled assays is triggered and simultaneously detection on the porous element in the light-tight compartment formed from the disposable device and the detector head. The signal is integrated over a period of time longer than the sum of the rise and decay time of the chemiluminescence signal, and longer than the residence time of the triggered reaction mixture in the porous element.

Alternatively, a sandwich immunoassay can be performed employing a polyanionic acid such as polyglutamic acid which is attached to the antibody and added to a reaction vessel, either simultaneously or sequentially, with an enzyme-labeled antibody or antigen. Alkaline phophatase or β-galactosidase-labeled antigen or antibody may be used. The reaction mixture is incubated for a period of time and under conditions which maximize the specific binding reaction. The reaction mixture is similarly transferred to a separation and detection chamber as described above and a chemiluminescent indicator added thereto to generate a chemiluminescent signal from the porous element in the separation and detection chamber before it is mated with the detector head to form the light-tight compartment where the chemiluminescence signal is detected. The signal is integrated over a period of time that is generally shorter than the residence time of the luminescent reaction mixture in the porous element.

According to the present invention, incubation and separation steps take place in two independent compartments. This limits the time during which the sample and conjugate are in contact with the porous element and the walls of the detection compartment. Thus the amount of sample and labeled reagent that binds non-specifically to the porous element and the wall of the separation and read compartment is substantially reduced as compared to incubation, wash and detection in the same well, as described in U.S. Pat. No. 4,652,533, *J. Immuno. Methods,* 67, 21-35 (1984), or *Clin. Chem.* 32, 1682-1686 (1986), and, accordingly, improves assay sensitivity.

A preferred device for performing the incubation and transferring the reaction mixture into the read well is that described in a co-pending U.S. patent application entitled "Automated Method and Device for Performing a Solid Phase Chemiluminescent Assay" Ser. No. 07/425,651, filed on even date herewith, incorporated by reference herein. Such device comprises a funnel-like structure, a porous element, and an absorbant material, which are assembled to provide intimate contact between the porous element and the absorbant material, as well as adequate venting of air displaced by fluids absorbed in said absorbant material. The capacity of the absorbant material is chosen to be larger than the total volume of sample, reagents and wash solution used in the assay steps. This ensures adequate washing of the retained reaction product, prevents excessive fluid retention on the porous element, and helps to protect the detection device against possible trigger solution splashing. The funnel-like structure and the porous element are parts of the light-tight compartment formed when the device is mated with said detector head of the present invention to detect a chemiluminescence signal generated on the porous element.

It is to be understood that one skilled in the art can design other reaction vessels that incorporate a porous element for retaining the reaction complexes of an immunochemical reaction as described herein, other means for transferring the reaction mixture and other means for disposing of the excess reagents and wash solution such as vacuum and pressure means, that can be used with the detector head of the present invention.

An example of the chemiluminescence detection device is illustrated in FIG. 1. The detector device consists of a frame (4), a detector head (5), a flexible diaphragm (6), and a lifter mechanism (7). The frame allows mounting the detector assembly on a thermostated tunnel where a timing belt moves a plurality of disposable reaction devices at a given step rate. The detection head (5) consists of a shroud (10), and ports for fluid lines (11,12). The lifter mechanism (7) moves shroud (10) up and down on a Z-axis. The down movement affects a light seal with the separation and detection chambers of a disposable tray where a chemiluminescence signal is generated and detected, and the upward movement is to clear the disposable to allow its free movement to the other positions at the end of measurement.

Figure 2:
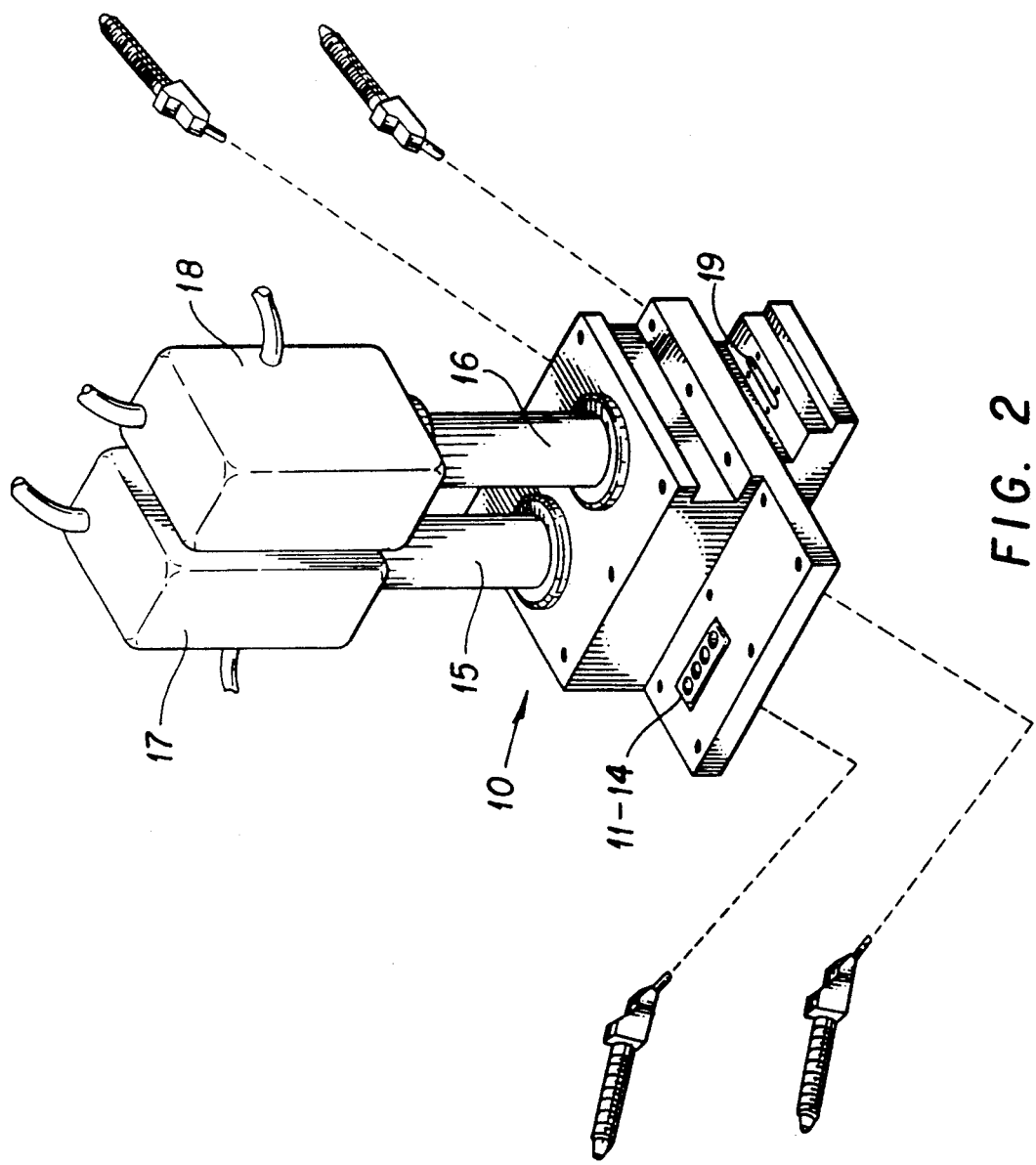

FIG. 2 shows an isometric view of a preferred configuration of the detection apparatus that is designed to accommodate the preferred disposable reaction tray of co-pending U.S. patent application entitled "Automated Method and Device for Performing A Solid-Phase Chemiluminescent Assay" Ser. No. 07/425,651, filed on even date herewith and incorporated by reference herein, which contains two rows of separation and read wells at a 36 mm center to center distance. It is to be understood, of course, that one skilled in the art can redesign the envelope of the detection head to mate with other shapes of disposable devices.

The shroud (10) is made from machined aluminum or cast polyurethane, and comprises four ports for trigger solution injection outlets (11–14), two optical detection modules (15, 16), and two boxes (17, 18) containing photon counting amplifiers and electric leads for antifog heaters (19). Attached to shroud (10) is a flexible black rubber diaphgram (6) of FIG. 1 that allows the free vertical movement of the shroud (10).

Figure 3:
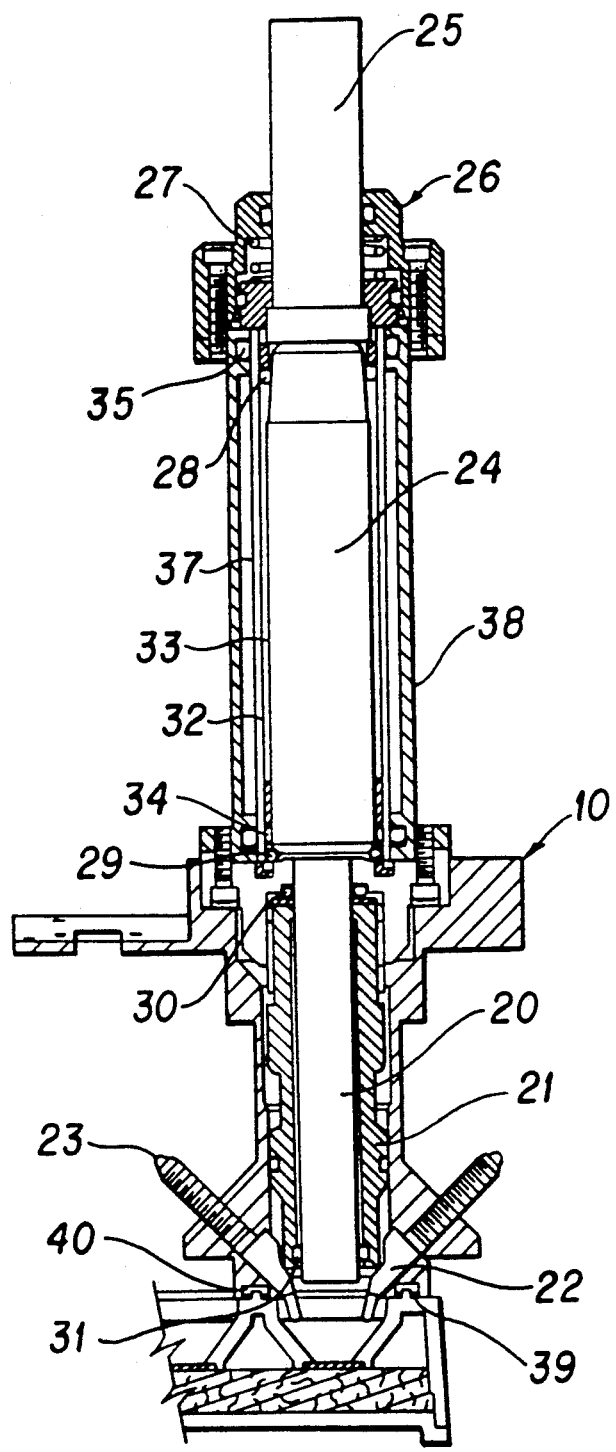

A cross-sectional view of the signal detection module is shown in FIG. 3 and comprises a light guide (20), light-pipe protecting sleeve (21), injectors (22, 23) that are connected to two of the black Teflon ® fluid lines (11–14) of FIG. 2, photomultiplier tube (PMT) (24), a photomultiplier tube socket (25) and a collar for holding the PMT socket (26). The PMT is springloaded by a 302 stainless steel spring wire (27) to ensure proper spacing from the light pipe and is protected from moisture by two O-ring seals (28 and 29). O-rings (30 and 31) fix the light pipe (20) in space and protect the face of the PMT from moisture. O-ring (30) is preferably made of a material with high dielectric constant to prevent Ohmic leakage at the photocathode. A mumetal shield (32) surrounds the PMT, with a nylon spacer (33) inside (32) which protects the PMT during assembly. The mumetal shield (32) is kept electrically isolated by use of two O-rings (34,35) and a Teflon sleeve (37) to separate it from the outer housing. An electrically conducting outer housing (38) protects the detection module. The bottom of shroud (10) has a groove (39) that locates the surface feature on the disposable device and a light sealing gasket (40) of FIG. 4. The light sealing gasket is made of black inert compressable polymer. A preferred material is a nylon nap on a rayon backing COE7-1673 (Schlegal Corporation, Rochester, N.Y.). Two low wattage anti-fog heaters (41, 42), are used to create a temperature gradient in the vicinity of the light pipe to prevent any condensation on the light pipe during the measurement.

Figure 4:
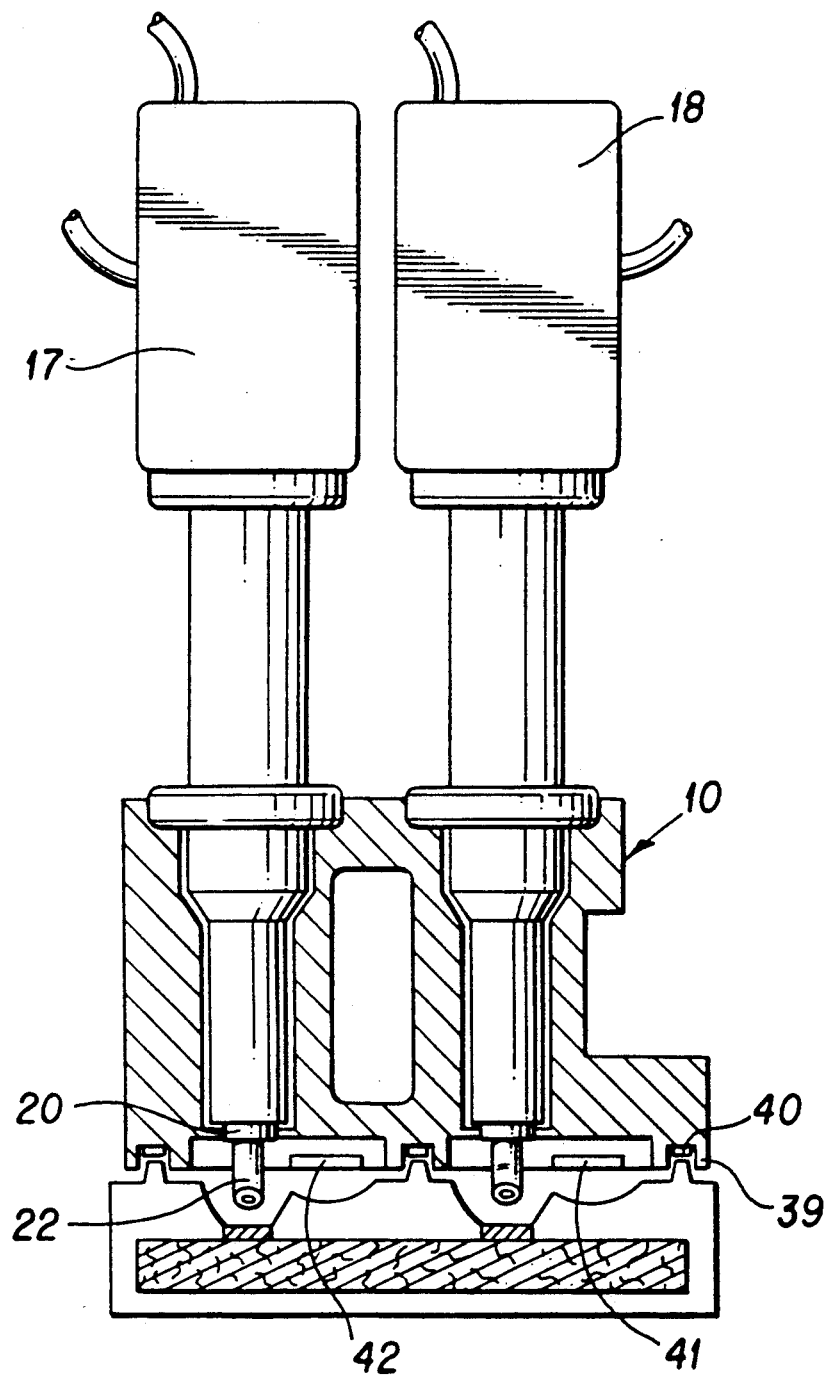
Figure 5:
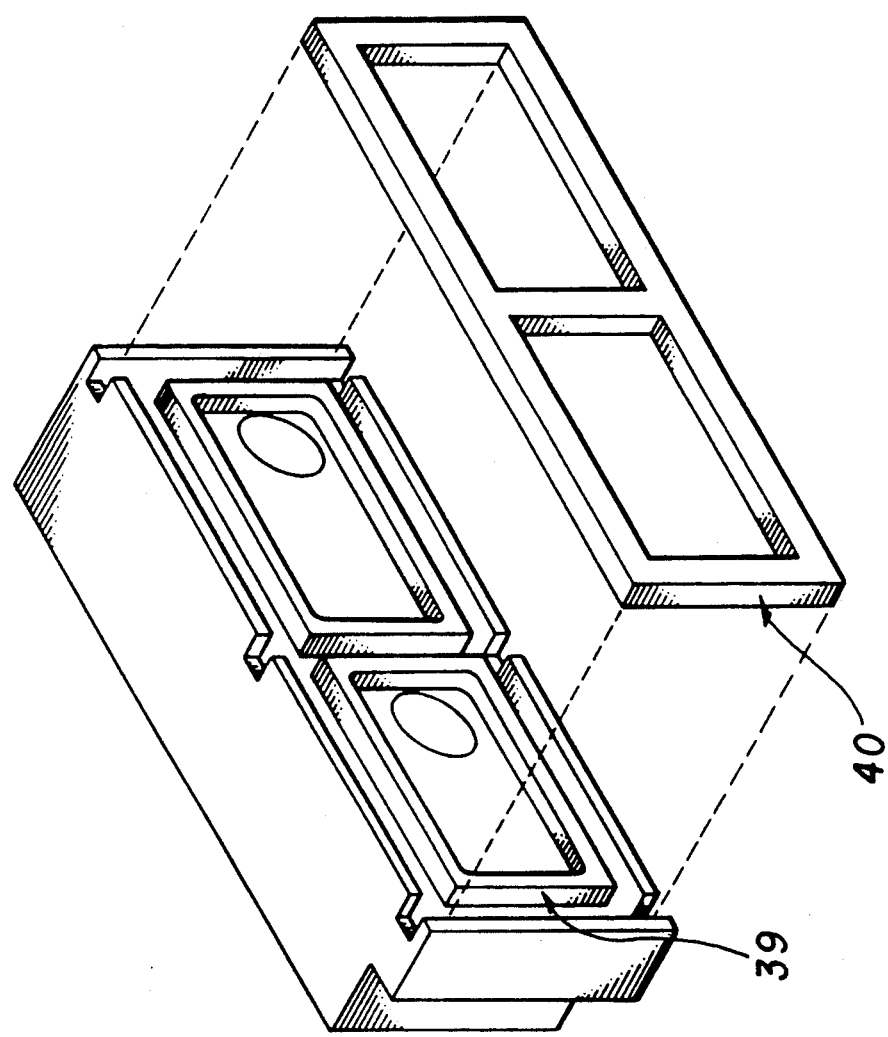

FIG. 4 is a cross-sectional view taken along the side of the detector device of the present invention and shows the two detector assemblies, shroud (19), groove (39) and light sealing gasket (40), the anti-fog heating elements (41, 42) and the end of an injector tip (22). FIG. 5 is an exploded view of the bottom of the shroud (10), showing the light seal groove (39) and the light sealing gasket (40).

Figure 6:
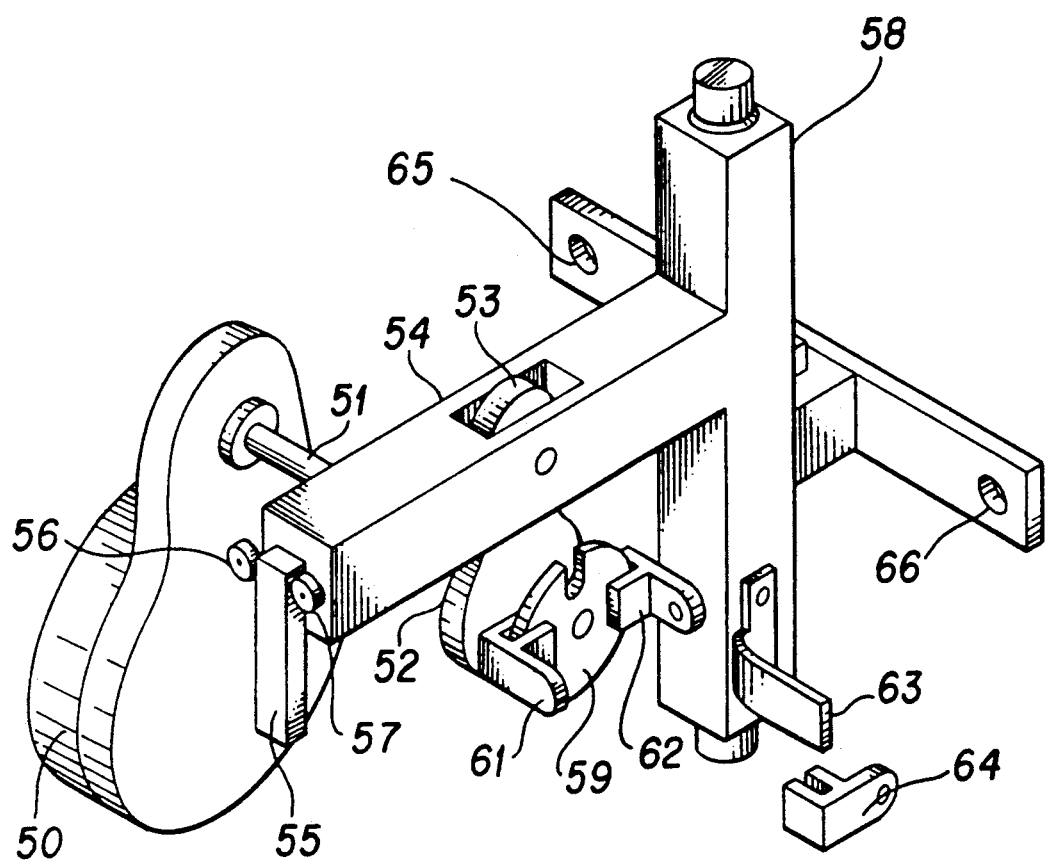

The lifter mechanism assembly (7) of FIG. 1 is shown in FIG. 6 and comprises an AC permanent magnet synchronous motor (50), a stainless steel shaft (51) and a cam (52) to control the vertical displacement of lifter. A stainless steel cam follower roller (53) mounted in the lifter arm (54) is in contact with the cam. A stainless steel guide bar (55) is part of the base and is in combination with stainless steel rollers for guide bar (56, 57). The stainless steel port or shaft (58), guide bar (55) and guide bar rollers (56, 57) ensure precise movement along the Z-axis without X or Y movements or rotation around the Z-axis. A slotted aluminum disk (60) and two diametrically opposed opto-sensors (61, 62) to control motor stops for full-up and full-down shroud positions. Shroud down flag (63) and shroud down sensor (64) ensure the engagement of the detector head with the disposable device. Holes (65, 66) are attachment points to the shroud (10) of FIG. 2.

As shown in FIG. 3, the terminuses of the injection ports (22, 23) are directed towards the walls of the detection chamber. The distance these ports protrude beyond the lower surface of the light pipe (20) is 0.213 inches. The lower end of the light pipe (20) is 0.435 inches above the surface of the porous matrix. Light pipe (20) is 8 mm in diameter and may be made of a quartz, glass or polished plastic rod having a length of approximately 3 inches long.

Figure 7:
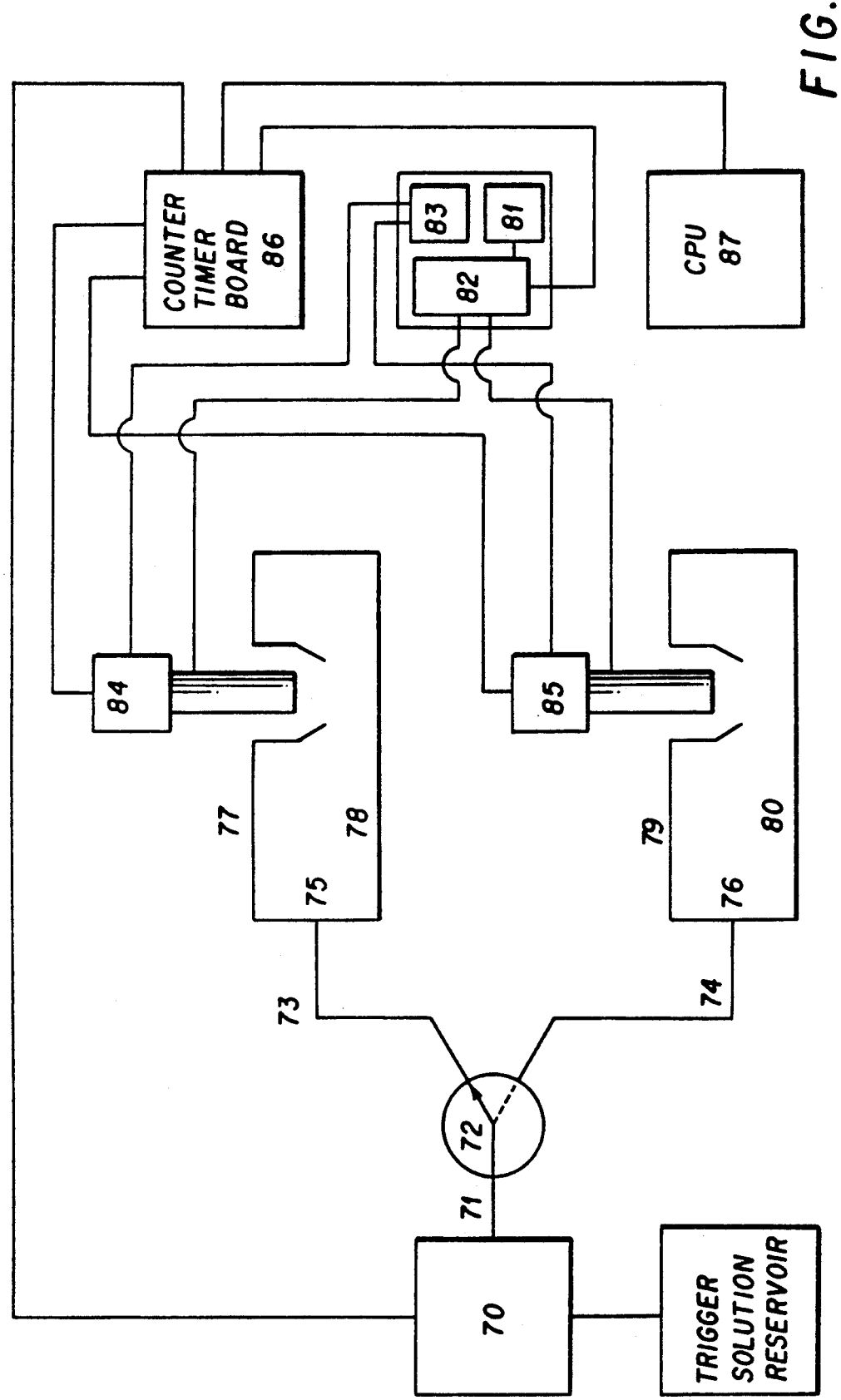

As indicated in FIG. 7, a trigger solution injection device (70) is used such as, for example, a piston pump such as FMI RH pump (Fluid Metering Inc., Oyster Bay, N.Y.). A Teflon ™ tube (71) having an inner diameter of 0.03 inches and an outer diameter of 0.062 inches (Cole Palmer, Chicago, Ill.) carried trigger solution from pump to a selonoid operated three way valve (72), [Angar Scientific, Florham Park, N.J.]. A trigger solution was diverted employing Teflon ™ tubes (73, 74) to two 2-outlet manifolds (75, 76). A Minstac multiport manifold (Lee Company, Westbrook, Conn.) was used. Two lines per manifold (77, 78) and (79, 80) made of Teflon ™ tubes having an inner diameter of 0.5 mm and an outer diameter of 1.59 mm (Aspect Inc., Ann Arbor, Mich.), carried the trigger solution from manifold to injection ports. For acridinium labeled chemiluminescence reactions, alkaline peroxide solution 80–100 $\mu$L was injected through the manifold onto separation and detection chamber at a rate of less than 500 $\mu$L per second.

The trigger solution was dispensed from two injector ports (22, 23), shown in FIG. 1, at 180 degrees to each other. Choosing an injection speed less than 500 $\mu$L per second through a 0.05 mm inner diameter injection prevented back-splash of the trigger solution towards the signal pick-up optics. This was verified by examination of high speed video recordings of the injection process.

A R647-04 head-on photomultiplier tube (24) (FIG. 3) and an E849-35 socket (25) and magnetic shield E989-09 (32) (Hamamatsu Inc., Middlesex, N.J.). The PMTs were powered to approximately 1040 V using a high voltage power supply (82) (FIG. 7) (Model PMT-20A/N Option 3, Bertan Associates, Hicksville, NJ). A ±12 V DC power supply (81) (FIG. 7) (Part#12EB50, Acopian Inc., Easton, Pa.) was used to power the high voltage power supply. The amplifier boards were powered by two isolated ±5 volts power supplies (83) (Part #5EB 100, Accopian Inc., Easton, Pa.).

The photon counting amplifier boards (84, 85) comprises a 12 MHz vidio amplifier MC 1733 CP (Motorola Inc., Semiconductors Division, Phoenix, Ariz.), an AM 686CN high speed comparator (Advanced Micro Devices, Sunnyvale, Calif.) is used as a discriminator, and the resultant TTL signal is divided by two using a 74F74 flip flop. The output drives a HFBR 1524 fiber optic transmitter (Hewlett Packard, Palo Alto, Calif.). The digital signal was carried on a fiber optic link to an HFBR-2524 fiber optic receiver, all are components of a HFBR-0501 kit from Hewlett Packard, Palo Alto, Calif. The fiber optic link carries the digital signal to the counter/time board, thus avoiding any noise pick-up or ground loop effects on this circuitry. The start count signal, integration time, trigger pump star/stop and trigger signal counting were controlled by the counter/timer board. The counter/timer board was designed and built using prior art designs and components. Those skilled in the art can easily design equivalent circuits.

The counter/timer board and the trigger solution pump are controlled by a micro computer as, for example, an IBM pc-XT (IBM Corporation, Boca Raton, Fla.), or an Intel 310 development system (Intel Corporation, Sunnyvale, Calif.) through a standard prior art interface.

Polyion-bound immune complexes are attracted to the oppositely charge porous element and then the porous element is washed with water or aqueous solution containing detergents and/or salt compositions to maximize efficiency of washing unreacted sample and label away from the porous element. Wash solution volume is chosen to be several times the volume of the reaction mixture, preferably about three times that volume. Wash solution composition is chosen to decrease non-specific binding and to increase assay sensitivity. Thus water, saline solution, or hypertonic buffered salt solutions can be used. Number of wash cycles are also important to assay sensitivity, thus applying multiple aliquots of wash solution is preferred. Prewetting the porous matrix with wash solution or a protein-containing solution may also help in decreasing non-specific binding and increasing specific binding.

The apparatus of the present invention can be used to detect shortlived alkaline peroxide triggered chemiluminescences such as acridinium label chemiluminescence or long-lived dioxetane chemiluminescence, such as described by WO 881 00694 and EP 0-254-051A2. In the case of short-lived chemiluminescence, activating the CL signal is affected within the light-tight compartment created by mating the detector device with the disposable device. Thus, trigger solution injector ports, fluid lines, manifolds and pumps are an integral part of the detection device. Long-lived dioxetane-type chemiluminescence is generated by adding an enzyme specific chemiluminescent substrate to the enzyme-labeled immune complex on the porous element. An example is the commercially available alkaline phosphatase substrate 3-(2'-spiroadamantane)-4-methoxy-4-(3'-phosphoroxy)phenyl-1,2-dioxetane disodium salt (AMPPD) from Tropix Inc., Bedford, Mass. The substrate can be incubated before the disposable device engages the detector head and start of signal integration. The total signal intensity is integrated over a portion of the intensity-time curve.

The acridinium sulfonamide labeled chmiluminescent reaction is triggered on the porous element by alkaline peroxide solution using the two injectors in the detection device. Trigger solution injection ports may be made from chemically inert material that is not affected by high alkaline peroxide concentrations. Preferred materials for fabricating these injectors are Teflon TM, Kel-F TM, nylon, ultra high molecular weight polyethylene or Teflon TM -coated stainless steel. The assembly of injectors, light guide and the porous element is light tight and the aperture of the light guide is in close proximity to the surface of the porous element. A preferred geometry is to have two trigger solution injectors at 180° to each other on the periphery of the light guide. The light guide may be made of optical quality plastic, glass, quartz or a highly polished hollow metallic tube. The light guide directs emitted chemiluminescence signal to the photo detector.

The trigger solution is directed towards the walls of the separation and detection chamber in the disposable and is injected at such a slow rate to minimize splashing of the fluid towards the light pick-up optics. Injection rates of less than 500 $\mu$L per second are preferred. The trigger solution flows down the walls of the detection chamber to the porous element from more than one direction to form a puddle of fluid that uniformly diffuses through the porous element.

The volume of trigger solution is chosen to be slightly larger than the fluid capacity of the porous element. Thus volumes in the range of 50-100 $\mu$L are preferred. Signal integration times longer than the residence time of the triggered reaction mixture in the porous element are used. The chemiluminescent reaction takes place on the surface of the porous element as well as from in the interstice of porous element.

Hydrogen peroxide concentration in the alkaline peroxide solution used to trigger the chemiluminescent reaction on the porous element is kept at 0.1-1.0% by volume in 0.25N sodium hydroxide solution. A preferred concentration is 0.3% hydrogen peroxide solution in 0.25N sodium hydroxide solution. Typically chemiluminescent reactions in solution are triggered with alkaline hydrogen peroxide containing approximately 0.03% by volume hydrogen peroxide in 0.1-0.25N sodium hydroxide solution. Higher peroxide concentrations of the trigger solution generate higher signal in a short period of time before triggered reaction mixture diffuses through the porous element.

Alkaline phosphtase/dioxetane chemiluminescence can be triggered outside the detector head and the signal is collected after the enzyme substrate reaction reaches a steady state. In this case trigger solution pump, lines and injectors are not used. Signal is collected after the detection head mates with the disposable as is indicated by a signal from the shroud-down sensor. Alternatively the signal is collected in a rate mode. The trigger solution pump and lines can be used to deliver the substrate solution and the change in CL intensity as a function of time is calculated by performing a series of short duration readings over a period of time. Preferred enzyme labels and substrates are alkaline phosphatase and 3-(2'-spiroadamantane)-4-methoxy-4-(3''-phosphoryloxy)phenyl-1,2-dioxetane (AMPPD) substrate. $\beta$-galactosidase can also be used as a label and 3-(2'-spiradamantane)-4-methoxy-4-(3''-$\beta$-D'-galactopyrano-yloxy)phenyl-1,2-dioxetane (AMPGD) can be used as a substrate.

The light pipe directs emitted chemiluminescent signal to a photomultiplier tube and detection electronics. A preferred signal collection method is the use of single photon counting techniques. Detecting low light level signals is known to those skilled in the art. Cooled photodiodes, avalanche photodiodes, intensified vidicon tubes or microchannel plates can be substituted for the photomultiplier tub without deviation from the spirit of the invention. A preferred light guide configuration is a highly polished quartz rod 8 mm in diameter and 0.5- to 3 inches long. The length of the light pipe is not important as it is chosen for packaging convenience. Other light guide configurations such shaping the end of the rod to encompass a lens-like structure, use of a prism shaped terminus, use of fiber optic bundle or gradient index lens can be contemplated and applied by those skilled in the art and does not deviate from the spirit of this invention.

The present invention will now be illustrated, but is not intended to be limited, by the following examples:

EXAMPLE I

Precision Activating And Measuring Short-Lived Acridinium Chemiluminescence In A Glass Fiber Matrix The precision of measuring a short-lived chemiluminescence signal in a porous element was determined as follows:

50 μL of acridinium labeled anti-HBC antibody conjugate solution (Hepatitis B Core antigen Clinical Lots) were manually dispensed on a glass fiber matrix in each of 16 separation and detection wells of a disposable reaction tray such as described in a co-pending U.S. patent application entitled "Automated Method and Device for Performing A Solid-Phase Chemiluminescent Assay 07/425,651, filed on even date herewith and incorporated by reference herein. Trigger solution was prepared by dissolving tablets containing urea peroxide in 0.25M sodium hydroxide to yield effective peroxide concentration of 0.3%. The tray was moved under the detector head device of the present invention. The detector head was lowered to mate with the first two wells of the disposable tray and create a light-tight compartment. The high voltage to the PMTs are gated on and allowed to equilibrate for 3 seconds. Dark counts were then collected on one of the PMTs for 6 seconds. The trigger pump was activated and the valve directed the trigger solution to the separation and detection well under this PMT. 85 μL of 0.3% alkaline peroxide solution were injected through the two injectors and the triggered signal integration started simultaneously and continued for 6 seconds integrating. The dark counts of the second PMT was then started for 6 seconds followed by activating and simultaneously counting the chemiluminescence signal for 6 seconds. The detector head was then lifted upward to clear the tray and the tray advanced so that two new wells were located under the detector head. The detector head was lowered and the process of dark count and triggered counts was repeated on the rest of the 8 rows of wells on the disposable reaction tray. The data is shown in Table 1.

TABLE 1

Precision Activating And Measuring Short-Lived Chemiluminescence From Acridinium Labeled Anti-HBC In A Glass Fiber Matrix

|  | Side A | | Side B | |
| --- | --- | --- | --- | --- |
|  | Dark counts | Trigger counts | Dark counts | Trigger counts |
|  | 39 | 38275 | 37 | 35548 |
|  | 29 | 40177 | 38 | 34476 |
|  | 57 | 40244 | 34 | 34348 |
|  | 31 | 39742 | 31 | 34650 |
|  | 39 | 40141 | 31 | 34952 |
|  | 35 | 39615 | 38 | 33780 |
|  | 35 | 40306 | 32 | 34990 |
|  | 28 | 39839 | 41 | 34523 |
| Mean | 37 | 39792 | 35 | 34658 |
| SD | 9 | 663 | 6 | 186 |
| % CV |  | 1.7 |  | 1.5 |

The low dark counts indicate that a light tight seal has been achieved between the disposable device and the detector head. The low % CV indicate the reproducibility of activating and detecting a short-lived chemiluminescence signal within a porous element.

EXAMPLE II

Reproducibility Activating And Measuring A Chemiluminescent Signal From Luminescent Microparticles Immobilized On a Porous Element Acridinium sulfonamide labeled antibody to Heptatitis B core antigen (pooled, 5 μg/mL), was diluted in conjugate diluent, containing 50% fetal calf serum (Abbott Laboratories, North Chicago, Ill.) 2% human plasma, 0.1% Tween ®-20, 0.1% ethylenediamine tetra acetic acid and 0.1% sodium azide in phospate buffered saline, pH 6.8. The final conjugate concentration was 150 ng/mL. Carboxylated polystyrene microparticles coupled to antibody to Hepatitis B core antigen as an undercoat and then with recombinant Hepatitis B core antigen were pooled from lots prepared for clinical trials and contained 0.3% solids by weight. Microparticles were suspended in phosphate buffered saline (Abbott Laboratories, North Chicago, Ill.), pH 7.2, containing 16% sucrose. A 0.1% solution of Tween ®-20 in phosphate buffered saline, pH 7.2, was used as a transfer solution. Luminescent microparticles were prepared by mixing 50 mL of conjugate solution and 50 mL of microparticles suspension. The reaction mixture was incubated in a water bath at 40° C. for two hours. It was then let stand at room temperature for 24 hours to ensure complete binding of acridinium sulfonamide labeled antibodies to the antigen labeled microparticles.

100 μL of luminescent microparticles were dispensed on the porous fibrous glass matrix in each of the 16 read wells of a disposable reaction tray as described in Example 1 were allowed to drain through. The microparticles were washed with 100 μL of fetal calf serum, 100 μL of de-ionized water and two aliquots 300 μL each of a 0.1% Tween ®-20 solution. The disposable tray was linearly moved to a subsequent position where the chemiluminescence detection head of the present invention was lowered to create a light tight seal with the disposable tray. The immobilized and washed microparticles on the glass fiber matrix were triggered using 0.3% alkaline peroxide solution and the resulting chemiluminescence signal was integrated for a period of six seconds. The mean and standard deviation for each eight wells on each side of the disposable were calculated.

TABLE 2

Reproducibility Activating And Measuring A Chemiluminescent Signal From Luminescent Microparticles Immobilized On A Porous Element.

|  | Side A | | Side B | |
| --- | --- | --- | --- | --- |
|  | Dark counts | Trigger counts | Dark counts | Trigger counts |
|  | 37 | 53023 | 42 | 49956 |
|  | 40 | 54573 | 47 | 49473 |
|  | 38 | 54214 | 52 | 49473 |
|  | 45 | 54664 | 34 | 48586 |
|  | 43 | 55471 | 37 | 47624 |
|  | 44 | 55446 | 43 | 47624 |
|  | 42 | 55084 | 54 | 47898 |
|  | 62 | 54450 | 44 | 48053 |
| Mean | 44 | 54616 | 44 | 48588 |
| SD | 7 | 234 | 7 | 220 |
| % CV |  | 1.4 |  | 1.8 |

The low dark counts indicate that as light tight seal has been achieved between the disposable device and the detector head. The low % CV indicate the reproducibility of entrapping luminescent microparticles and of activating and detecting a short-lived chemiluminescence signal within a porous element.

EXAMPLE III

Microparticle-Based Sandwich CLIA for Hepatitis B Surface Antigen

An Ay and an Ad sensitivity panels and positive and negative controls for Hepatitis B Surface antigen (Abbott Laboratories, North Chicago, Ill.) chemiluminescence conjugate acridinium labeled goat polyclonal antibody (0.17 µg/mL) was employed.

A conjugate diluent was prepared comprising 0.1M monosodium phosphate, 0.1M disodium phosphate, 0.1% sodium azide and 53% calf serum (Abbott Laboratories North Chicago, Ill.), 10% normal human serum and was filtered through 0.45 µm Nalgene disposable sterile filter (Nalge Company, Division of Sybron Corporation, Rochester, N.Y.). It was adjusted to a final pH of 6.3 and finally filtered through a 0.2 µm Nalgene Filter.

Carboxylated polystyrene microparticles (0.21 µm) were coupled to IgM anti-HBsAg antibodies using EDAC coupling procedure, and having a total solids content of 0.24%.

The washing solution contained 0.1M borate, 0.02% lithium dodecyl sulfate, 0.9% sodium chloride and 0.1% sodium azide.

200 µL of control or sample were pipetted into the shallow reaction wells of a disposable tray as described in Example 1 using an automatic pipettor. 30 µL of latex particles coated with monoclonal IgM mouse-antihepatitis B surface antigen were dispensed into each incubation well. The reaction mixture was incubated for 20 minutes in a heated tunnel at 40° C. with the disposable device moving into the tunnel by a timing belt at increments of 0.8 inches per assay step. It remains in position for 72 seconds for performing an assay step, then it increments again at 0.8 inches for the next assay step.

The reaction mixture was transferred and washed from shallow incubation well onto the glass fiber matrix of read well, by injecting two pulses 300 µL each of the wash solutions using the method of transfer as described herein. After the transfer and wash solution has drained down the absorbant pad, 30 µL acridinium labeled polyclonal goat anti human HBS antibodies were dispensed on each fibrous pad. The disposable was moved on the timing belt to allow subsequent well pairs to pass under the transfer device and to affect transfer of the reaction mixture. The disposable tray was incubated for 30 more minutes in the tunnel using the same moving timing belt as it is moved to a washing position. The transferred microparticles that are retained on the glass fiber matrix and the added acridinium labeled antibodies were subsequently washed with three aliquot, 100 µL each of wash solution containing 0.1% sodium dodecyl sulfate, from a wash nozzle. The disposable tray was moved at the same rate to a read position where the chemiluminescence detection head of the present invention was lowered to mate with the surface feature of the first two wells on the disposable to create a light-tight seal. The transferred and washed microparticles were triggered using 0.3% alkaline peroxide solution. The measured signal for each well was considered to correspond to the amount of acridiniium labeled conjugate attached to the microparticles and hence directly related to the concentration of the Hepatitis B surface antigen in the sample.

TABLE 3

Microparticle Capture Chemiluminescence Immunoassay for Hepatites B Surface Antigen: Sensitivity Panel Data.

| Member | Concentration ng/mL | Counts/6 secs | % CV |
|---|---|---|---|
| ADA | 1.90 | 19270 | 5.8 |
| ADB | 1.48 | 15659 | 6.2 |
| ADC | 0.92 | 10756 | 7.1 |
| ADD | 0.74 | 8945 | 4.9 |
| ADE | 0.51 | 6717 | 5.2 |
| ADF | 0.41 | 5751 | 5.3 |
| ADG | 0.31 | 4547 | 2.1 |
| ADH | 0.10 | 2840 | 4.2 |
| AYA | 2.05 | 23751 | 4.5 |
| AYB | 1.11 | 14242 | 3.7 |
| AYC | 0.83 | 11216 | 4.9 |
| AYD | 0.67 | 8455 | 2.2 |
| AYE | 0.53 | 7132 | 4.7 |
| AYF | 0.44 | 6295 | 4.8 |
| AYG | 0.30 | 4926 | 4.9 |
| AYH | 0.14 | 2911 | 4.0 |
| Negative Control | | 1247 | 8.3 |
| Positive Control | | 115219 | 6.1 |

The standard deviation for twelve replicates of the negative control was 104. The cut-off value of the assay calculated by adding 10 standard deviation to the mean of the negative control was 2287 counts. Thus, concentrations of Hepatitis B Surface Antigen as low as 0.10 ng/mL of the AD subtype and 0.14 ng/mL of the AY subtype can be quantified using a microparticle capture chemiluminescence immunoassay and the method and device of the present invention. Using the same criterion to the data published in Table 4 of *Clin. Chem.* 27, 1378-1384 (1981), yields a lowest limit of quantitation of 5 mg/mL. Thus, a limit of quantitation of Hepatitis B surface antigen one order of magnitude lower than reported using prior art techniques can be achieved using the device and method of this invention.

EXAMPLE IV

Ion-Capture Alkaline Phosphatase Labeled Chemiluminescence Competitive Binding Immunoassay For a Hapten This example shows the use of the detection device and method of this invention in a competitive binding assay for the abused drug phenylcyclidine (PCP). This assay is performed on urine specimens and uses the ion capture immunoassay procedure described herein. The formation of the immune complex involves the use of an anionic polymer as a capture agent. The reaction mixture is transferred to the detection well of said device and the product of the immunochemical reaction is immobilized by ionic forces on a porous plug that has been previously treated with a solution of a cationic polymer to render it positively charged.

Anti-phenylcyclidine antibodies were labeled with alkaline phosphatase using art procedures known in the art. The labeled antibody solution was diluted in a solution containing 1% fish gelatin, 25 mM Tris, 100 mM sodium chloride, 1 mM magnesium chloride, 0.1 mM zinc chloride, and 0.1% sodium azide. The pH of the solution was 7.2 Prewet and transfer solutions were IMx buffer (Abbott Laboratories, North Chicago, Ill.) containing 25 mM Tris, 0.3M sodium chloride, 0.1% sodium azide, pH 7.2. The cationic polymer was a 0.5% aqueous solution of Celquat TM L-200 (National Starch and Chemical Company; Bridgewater, N.J.) in 10 mM sodium chloride.

The capture agent, phenylcyclidine-polyglutamic acid, was prepared as follows:

1 gm of polyglutamic acid sodium salt (Sigma Chemical Company, St. Louis, Mo.) was added to 7 gms of AG50W-X8 ion exchange resin (Bio-Rad, Richmond, Calif.) in 20 mL water and stirred overnight. Liquor was removed and lyophilized to give free acid polyglutamic acid (PGAFA).

Phenylcyclidine-4-chloroformate was prepared by reacting 1.1 mg 4-hydroxyphenylcyclidine ($4.24 \times 10^{-6}$ moles) in 0.5 mL tetrahydrofuran with 0.5 mL of 10% solution of phosgene in benzene (130 mole excess). The reaction was allowed to proceed for 2.5 hours at room temperature. Solvent was evaporated under a stream of nitrogen to yield a residue of phenylcyclidine-4-chloroformate. The residue was dissolved in 0.5 mL tetrahydrofuran and 1.7 mg of free acid polyglutamic acid (molecular weight 40,000) in 0.5 mL 1-methyl-2-pyrrolidinone was added to it. The reaction was carried out overnight at room temperature then the reaction mixture was evaporated to dryness. The dried mixture was dissolved in 1.5 mL 0.1M phosphate buffer, pH 7.0 and dialyzed against a volume of the same buffer in a 3,500 molecular weight cut-off dialysis bag. The precipitate was filtered. The cloudy aqueous filtrate was extracted with methylene chloride until it was clear. The aqueous layer was diluted in a buffer containing 1% fish gelatin, 25 mM Tris, 100 mM sodium chloride, 1 m magnesium chloride, 0.1 mM zinc chloride and 0.1% sodium azide at pH 7.2 to yield 5 5.0 μgmPGA/mL phenylcyclidine-PGA capture reagent.

Sample were phenylcyclicidine calibrators from a TDx TM fluorescence polarization immunoassay kit (Abbott Laboratories, North Chicago, Ill.). Containing 250, 120, 60, 25, and 0 ng/mL phenylcyclidine in human urine as confirmed by independent analytical methods. The glass fiber matrix of a disposable reaction tray as described herein was treated with 50 μL of a 0.5% Celquat TM L-200 (National Starch and Chemical Company, Bridgewater, N.J. 08807) in a 10 mM solution of sodium chloride. The Celquat TM L-200 solution was manually applied to each glass fiber matrix. 150 μL sample (PCP calibrators), 45 μL IMx buffer, and 420 μL alkaline phosphatase labeled antiphenylcylildine antibody solution were incubated in test tubes in a water bath at 37° C. for 10 minutes. 300 μL of the phenylcyclidine polyglutamic acid capture reagent and 45 μL IMx buffer were added to the reaction mixture and incubated for 10 more minutes at 37°C. 200 μL of the reaction mixture was manually transferred onto the treated glass fiber matrix of the reaction tray using a manual pipettor. The excess reagents were washed by manually dispensing two 75 μL aliquots of IMx buffer on the porous fibrous glass plug. 100 μL of a chemiluminescent substrate, 3-(2'-spiroadamantane)-4-methoxy-4-(3''-phosphoroxoy)phenoxy)phenyl-1,2-dioxetane disodium salt (AMPPD) in a 50 mM sodium bicarbonate solution containing 1 mM magnesium chloride at a pH of 9.5, was dispensed onto the glass fiber matrix using an FMI-RH pump (Fluid Metering Inc., Oyster Bay, N.Y.) and was incubated in the glass fiber matrix for 10 minutes. The pump, track and detection head functions were controlled by an IBM PC/XT. Track stepper motor was controlled with a stepper motor controller board (Scientific Solutions, Solon, Ohio). The FMI pump was controlled through a Triac interface consisting of MOC 3031 Opto Triac Driver and MAC 3030-8 triac (Motorola, Inc., Semiconductor Division, Phoenix, Ariz.). The tray was then moved under the detector device of the present invention. Substrate dispensing and chemiluminescence signal detection were controlled in such a way that the substrate incubation time in all glass fiber matrices were the same. The detector head was lowered to mate with the disposable device and create a light-tight compartment for chemiluminescence measurement. The chemiluminescence was integrated for 6 seconds per well, as shown in Table 4.

TABLE 4

Ion-Capture Alkaline Phosphatase Labeled Chemiluminescence Competitive Binding Immunoassay for Phenylcyclidine in Urine.

| Phenylcyclidine [ng/mL] | Chemiluminescence signal counts/6 seconds | Net Polarization ΔmP |
|---|---|---|
| 0 | 3526 | 198 |
| 25 | 2162 | 173 |
| 60 | 1440 | 144 |
| 250 | 1016 | 82 |

The last column shows the change in degree of polarization of a PCP analog labeled with a fluorescein as it binds to anti-PCP antibody in a competitive binding assay in solution. The trend in the chemiluminescence signal of the entrapped product on the glass fiber matrix parallels that of fluorescence polarization techniques known in the art in solution using a commercially available fluorescence polarization analyzer (TDx Analyzer, Abbott Laboratories, North Chicago, Ill.) and commercially available fluorescence polarization kits (Abbott Laboratories, North Chicago, Ill.).

EXAMPLE V

Ion-Capture Acridinium Labeled Chemiluminescence Competitive Binding Immunnoassay for a Hapten The present example shows the use of the device and method of this invention in a competitive binding assay for the abused drug phenylcyclidine (PCP). This assay is performed on urine specimens and uses the ion capture immunoassay procedure as described herein. The immune complex was formed in the shallow reaction well of the disposable tray as described herein and involves the use of an anionic polymer as a capture agent. The reaction mixture was transferred to the read well of the device and the immunochemical reaction product was immobilized by ionic forces on the glass fiber matrix of the device which had been previously treated with a solution of a cationic polymer.

Monoclonal anti-phenylcyclidine antibody was labeled with acridinium sulfonamide using EDAC coupling procedures known in the art. It was kept in the same buffer used for the anti-core conjugate of Example 3. The prewet and transfer solutions were IMx buffer (Abbott Laboratories, North Chicago, Ill.) containing 25 mM Tris, 0.3M sodium chloride, 0.1% sodium azide, pH 7.2.

The cationic polymer was a 0.5% aqueous solution of Celquat TM L-200 (National Starch and Chemical Company; Bridgewater, N.J.) in 10 mM sodium chloride, and the anionic capture agent phenylcyclidinepolyglutamic acid was prepared according to the procedure of Example IV.

Samples were phenylcyclidine calibrators from a TDx TM fluorescence polarization immunoassay kit (Abbott Laboratories, North Chicago, Ill.). They contained 500, 250, 120, 60, 25, and 0 ng/mL phenylcyclidine in human urine. 80 μL of IMx Tris buffer solution followed by 80 μL Celquat TM L-200 solutions were dispensed on the glass fiber matrices of the disposable reaction tray. Solutions were dispensed using two FMI-RH pumps and controlled via a triac board by an Intel 310 Development System (Intel Inc., Sunnyvale, Calif.). The tray was moved on a linear track using a timing belt and a stepper motor. The stepper motor was controlled by a board employing components known in the art. After 4.8 minutes, 50 μL of calibrator (sample) was pipetted into the shallow reaction wells of a disposable reaction tray, using an automated pipettor. 50 μL of acridinium labeled anti-PCP antibodies was dispensed into each incubation well. The mixture was incubated for 9.6 minutes in a heated tunnel at 32° C. with the disposable device moving into the tunnel by the timing belt in steps at the rate of 0.8 inches per minute, the reaction tray being stationary for 36 seconds after each step for a reaction step to take place. After 9.6 minutes incubation on the moving timing belt, 50 μL a solution containing PCP-PGA capture reagent at a concentration of 1.9 mg PGA/mL was dispensed into the incubation well through a tip centered on the well. The capture reagent solution was dispensed by an FMI-RH pump and controlled by the 310 Development system through a triac interface board. The reaction mixture was further incubated for 9.6 minutes. The quaternary ammonium polymer-treated glass fiber matrices were rinsed with 100 μL of the IMx buffer before reaction mixture transfer.

As the disposable tray was positioned under the transfer device as described herein, the reaction mixture was transferred and washed from the shallow incubation well onto the pre-treated glass fiber matrix in the detection well. The disposable tray was moved on the timing belt to allow subsequent well pairs to be located under the transfer device and to affect transfer of the reaction mixture. The disposable device was then moved to a read position, where the chemiluminescence detection head of the present invention was lowered to mate with the surface feature on the first two wells on the disposable to create a light-tight seal. The retained and immobilized immune complex on the glass fiber matrix was triggered using 0.3% alkaline peroxide solution in 0.25M NaOH and the signal from each PMT/amplifier was controlled by a counter/timer board and each side was triggered with an independent pump. The photon counter signal was integrated for eight seconds. The measured signal for each well was considered to correspond to the amount of acridinium labeled conjugate attached to the glass fiber matrix surface by ionic forces. The data is shown in Table 5 and is expressed as the number of counts and as % inhibition. The last column shows the change in degree of polarization of a PCP analog labeled with fluorescent as it binds to anti-PCP antibody in a competitive binding assay in solution. The trend in the chemiluminescence signal of the entrapped product on the glass fiber matrix parallels that of prior art fluorescence polarization in solution using a commercially available fluorescence polarization analyzer (TDx Analyzer, Abbott Laboratories, North Chicago, Ill.) and commercially available fluorescence polarization kits (Abbott Laboratories, North Chicago, Ill.).

The cut-off if this assay was considered to be 25 ng/mL. The data (Table 5) indicate that all controls containing 25 ng/mL PCP or higher were well differentiated from the negative control which indicates the validity of the present invention.

TABLE 5

| Ion-Capture Competitive Binding Assay for Phenylcyclidine (PCP) in Urine | | | |
|---|---|---|---|
| PCP [ng/mL] | Signal Counts | % Inhibition | Net Polarization |
| 0 | 188329 | 0.00 | 198 |
| 25 | 50347 | 73.3 | 173 |
| 60 | 30839 | 83.6 | 144 |
| 120 | 23977 | 87.3 | 112 |
| 250 | 20379 | 89.2 | 82 |
| 500 | 19759 | 89.5 | 65 |

Although the present invention has been described in terms of a prefered embodiment, it is anticipated that various modifications and improvements will occur to those skilled in the art upon consideration of the present invention. Thus shape, material and color of the vessel, material of the porous element, material and shape of the absorbent material, shape and design of the light guide, type of detector and method of detection, type of peroxide used as urea peroxide or similar compounds, wash solution composition, prewet solution composition, and method of treating porous elements to decrease nonspecific binding and provide the necessary interactions between the immobilizable complex and the porous element according to the present invention, can all be optimized by those skilled in the art. Although examples were shown for one step sandwich and competitive assays, two and more step assays can be performed.

Microparticles used to perform the solid phase immunoassay are preferably selected to have an average diameter smaller than the average effective pore size of the porous element. Although the examples were given using carboxylated polystyrene particles, other particulate material can be used, such as polystyrene, polymethyl acylate, derivatized cellulose fibers, polyacylamide and the like.

The ion capture procedures were described using polyglutamic acid as the polyanion acid derivatized polycationic material and other methods of attachment of these compounds to the assay components or the porous element can be used.

Moreover, the assay method of this invention may be extended to smaller molecules or to nucleic acid probe assays. Furthermore, although the invention has been described using acridinium sulfonamide-labeled and alkaline phosphatase-labeled tracers, it may be extended to other acridin ium compounds or their analogs or even other luminescent compounds. For example, the read head design as described above may accommodate luminol type chemiluminescent immunoassays by using two ports for injecting trigger solution and two other ports for injecting a catalyst solution. It can also be extended to phenol-enhanced chemiluminescence assay.

Apparatus and methods according to the present invention may be employed in assays for the detection of viral particles, such as HBsAg or HIV particles, or fragments thereof. Macromolecular disease state markers, such as carcinoembryonic antigen ("CEA") and alphafetoprotein ("AFP") may also be detected, as may nutritional status markers, such as vitamin B12, folate and ferritin. Also usefully detected by the apparatus and according to the methods of the present invention are hormones (e.g., B-HCG, TSH, LH and FSH). bacteria (e.g. streptococci) nuclei acid species (e.g. DNA or RNA). The present invention is also useful in small molecular competitive binding assays such as those for T3, T4, free T4 and digoxin. Substances of abuse may be detected using the methods and apparatus according to the present invention.

Allergy testing may be carried out by attaching allergen extracts to microparticles forming protein-coated microparticles, which may be incubated with body fluid sample to capture specific IgE. In such an assay acridinium-labeled goat anti-human IgE may be employed as a conjugate which may be reacted with bound IgE, followed by washing, activating and reading of the result.

What is claimed is:

1. Apparatus for performing a chemiluminesecent assay comprising:
   an incubation chamber, wherein all or some reactant components are incubated;
   a container, separate from said incubation chamber, having an aperture;
   a solid, porous element in said container, said solid, porous element having an interactive property with a chemiluminescent moiety in a chemiluminescent assay wherein said chemiluminescent moiety is immobilized by said solid, porous element thereby preventing the migration thereof while permitting passage of other reaction components of said chemiluminescent assay;
   a porous absorptive material in said container which is chemically inactive with respect to a chemiluminescent activating reaction;
   means, adjacent said aperture, for evenly distributing to said porous element a chemiluminescent-activating solution for said chemiluminescent activating reaction, wherein said means comprises a plurality of ports disposed toward an inclined interior surface of said aperture;
   means for providing a light-tight seal around said container comprising a shroud for positioning a detection head around said container to create said light-tight seal; and
   means for photodetection adjacent said aperture.

2. The apparatus of claim 1 wherein said solid, porous element comprises a fibrous matrix.

3. The apparatus of claim 1 wherein said interactive property is a hydrophobic interaction between said chemiluminescent moiety and said solid, porous element.

4. The apparatus of claim 3 wherein said solid, porous element is treated with a hydrophobic reagent.

5. The apparatus of claim 1 wherein said interactive property is an ionic interaction between said chemiluminescent moiety and said solid, porous element.

6. The apparatus of claim 5 wherein said solid porous element is treated with a cationic reagent and said chemiluminescent moiety is treated with an anionic reagent.

7. A method for performing a chemiluminescent assay to determine the amount of analyte which may be present in a test sample, said method comprising the steps of:
   forming a reaction mixture comprising an analyte from a test sample with a chemiluminescent moiety in an incubation chamber, said chemiluminescent moiety capable of binding to said analyte as a function of the amount of analyte present in said test sample;
   transferring said reaction mixture from said incubation chamber to a container having a solid, porous element in said container, said porous element having an interactive property with said chemiluminescent moiety wherein said analyte bound to said chemiluminescent moiety is immobilized by said interactive property between said chemiluminescent moiety and said porous element to thereby prevent said chemiluminesent moiety from migrating from said porous element;
   distributing a chemiluminescent activating solution onto said porous element by means of a plurality of ports disposed toward an inclined interior surface of said container, said activating solution capable of reacting with said chemiluminescent moiety immobilized to said porous element to provide a chemiluminescent signal therefrom;
   light-sealing around said container; and
   measuring said chemiluminescent signal from said porous element.

8. The method of claim 7 wherein said distribution step comprises the step of activating a chemiluminescent reaction by applying an alkaline oxidizing solution to said porous element.

9. The method of claim 7 wherein said solid, porous element comprises a fibrous matrix.

10. The method of claim 7 wherein said interactive property is a hydrophobic interaction.

11. The method of claim 7 wherein said interactive property is an ionic interaction between said chemiluminescent moiety and said solid, porous element.

12. The method of claim 7 wherein said solid, porous element is treated with a hydrophobic reagent.

13. The method of claim 7 wherein said solid, porous element is treated with a cationic reagent and said chemiluminescent moiety is treated with an anionic reagent.

14. A method for performing a competitive chemiluminescent immunoassay to determine the amount of analyte which may be present in a test sample, said method comprising the steps of:
   forming in an incubation chamber a competitive reaction mixture (i) an analyte from a test sample, said analyte or a binding analog thereof labeled with a chemiluminescent moiety, and a binding partner for said analyte or (II) an analyte from a test sample, a binding partner for said analyte labeled with a chemiluminescent moiety, and an immobilizable form of said analyte or analyte thereof;
   transferring said reaction mixture from said incubation chamber to a container having a solid, porous element, said porous element having an interactive property with said binding partner or said immobilizable form of said analyte wherein said analyte or binding analog thereof bound to said chemiluminescent label is immobilized by said interactive property therebetween to thereby prevent said chemiluminescent moiety from migrating from said porous element;
   distributing a chemiluminescent activating solution onto said porous element by means of a plurality of ports disposed toward an inclined interior surface of said container, said activating solution capable of reacting with said chemiluminescent moiety immobilized to said porous element through said binding partner to provide a chemiluminescent signal therefrom;
   light-sealing around said container; and
   measuring said chemiluminescent signal from said porous element.

15. The method of claim 14 wherein said distributing step comprises the step of activating a chemiluminescent reaction by applying an alkaline oxidizing solution.

16. The method of claim 14 further comprising the step of prewetting said porous element prior to said immobilizing step.

17. The method of claim 14 wherein said solid, porous element comprises a fibrous matrix.

18. The method of claim 14 wherein said interactive property is a hydrophobic interaction between said chemiluminescent moiety and said solid, porous element.

19. The method of claim 18 wherein said solid, porous element is treated with a hydropholic reagent.

20. The method of claim 14 wherein said interactive property is an ionic interaction between said chemiluminescent moiety and said solid, porous element.

21. The method of claim 20 wherein said solid porous element is treated with a cationic reagent and said chemiluminescent moiety is treated with an anionic reagent.

* * * * *

UNITED STATES PATENT AND TRADEMARK OFFICE
CERTIFICATE OF CORRECTION

PATENT NO. : 5,089,424
DATED : February 18, 1992
INVENTOR(S) : Omar S. Khalil, et al It is certified that error appears in the above-indentified patent and that said Letters Patent is hereby corrected as shown below:

Column 3, line 13, delete "building" and insert --binding--.
Column 5, line 54, delete "time" and insert --times--.
Column 7, line 53, delete "shroud (19)" and insert --shroud (10).
Column 15, line 32, delete "Sample" and insert --Samples--.

Signed and Sealed this

Second Day of November, 1993

Attest:

BRUCE LEHMAN

Attesting Officer

Commissioner of Patents and Trademarks